United States Patent [19]

Kühle et al.

[11] 4,376,735
[45] Mar. 15, 1983

[54] N-(SULPHENAMIDO)-ACYL ISOCYANATES

[75] Inventors: Engelbert Kühle, Bergisch-Gladbach; Hermann Hagemann, Leverkusen, both of Fed. Rep. of Germany

[73] Assignee: Bayer Aktiengesellschaft, Leverkusen, Fed. Rep. of Germany

[21] Appl. No.: 329,961

[22] Filed: Dec. 11, 1981

[30] Foreign Application Priority Data

Dec. 30, 1980 [DE] Fed. Rep. of Germany ....... 3049448

[51] Int. Cl.$^3$ .................. C07C 145/02; C07C 161/00
[52] U.S. Cl. ............................ 260/453 RW; 546/306; 549/480
[58] Field of Search ................ 260/453 RW; 546/306; 549/480

[56] References Cited

U.S. PATENT DOCUMENTS 3,344,153 9/1967 Kuhle et al. ............ 260/453 RW X
3,652,630 3/1972 Brown ......................... 260/453 RW

FOREIGN PATENT DOCUMENTS 7439 2/1980 Fed. Rep. of Germany .

OTHER PUBLICATIONS

Chemische Berichte, 99 Jahrg, Nr. 10, 1966, pp. 3063, 3103-3107.

Primary Examiner—Dolph H. Torrence
Attorney, Agent, or Firm—Sprung, Horn, Kramer & Woods

[57] ABSTRACT

Novel N-(sulphenamide)-acyl isocyanates of the formula

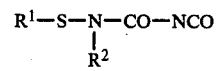

in which
$R^1$ represents a thrihalogenomethyl radical and
$R^2$ represents an aliphatic, cycloaliphatic, araliphatic, aromatic or heterocyclic radical
are useful as intermediates for reaction with amines to produce the corresponding fungicidally active biurets.

12 Claims, No Drawings

N-(SULPHENAMIDO)-ACYL ISOCYANATES

The present invention relates to certain new N-(sulphenamido)-acyl isocyanates, to a process for their preparation and to their use as intermediate products for the synthesis of fungicides.

The present invention provides, as new compounds, the N-(sulphenamido)-acyl isocyanates of the general formula $$R^1-S-N(R^2)-CO-NCO \quad (I)$$

in which
 $R^1$ represents a trihalogenomethyl radical and
 $R^2$ represents an aliphatic, cycloaliphatic, araliphatic, aromatic or heterocyclic radical.

The invention also provides a process for the preparation of a compound of the formula I, in which a trihalogenomethane-sulphenamide of the general formula $$R^1-S-NH(R^2) \quad (II)$$

in which $R^1$ and $R^2$ have the abovementioned meanings, is reacted with chlorocarbonyl isocyanate, of the formula $$Cl-CO-NCO \quad (III),$$

if appropriate in the presence of a diluent, in the temperature range of from 0° to 150° C.

The compounds of the formula I are interesting intermediate products for the preparation of plant protection agents having a fungicidal action.

It is surprising that the reaction according to the invention, in which hydrogen chloride is split off, should take place, since it is known that sulphenamides are easily cleaved by hydrogen chloride to give sulphenyl chlorides (see Chem. Ber. 57, 755 (1924); J. Gen. Chem. USSR (English translation) 29, 2129 (1959)). Accordingly, it would have been expected from the prior art that the evolution of hydrogen chloride which takes place at an elevated temperature would cause splitting off of the sulphenyl radical.

Preferred N-(sulphenamido)-acyl isocyanates of the general formula I include those in which
 $R^1$ represents a trichloromethyl, fluorodichloromethyl, difluorochloromethyl or trifluoromethyl radical and
 $R^2$ represents a straight-chain or branched alkyl radical with 1 to 18 carbon atoms, which can optionally carry one or more substituents selected from alkoxy with up to 4 carbon atoms, alkylmercapto with up to 4 carbon atoms, halogen, cyano and nitro, or represents an alkenyl or alkynyl radical, in either case with 3 to 8 carbon atoms, or represents a cycloaliphatic radical with 5 to 8 carbon atoms, which can optionally be substituted by alkyl with 1 to 4 carbon atoms, or represents an araliphatic radical with a total of 7 to 12 carbon atoms, of which the aromatic ring system can optionally carry one or more substituents selected from halogen, nitro, trifluoromethyl, cyano, alkyl with up to 4 carbon atoms and alkoxy with up to 4 carbon atoms, or represents an aromatic radical with 6 to 12 carbon atoms, which can optionally carry one or more substituents selected from halogen, nitro, cyano, alkyl with up to 4 carbon atoms, halogenalkyl with up to 4 carbon atoms, halogenalkoxy with up to 4 carbon atoms, alkylthio with up to 4 carbon atoms, halogenalkylthio with up to 4 carbon atoms and alkoxy with up to 4 carbon atoms, or represents a heterocyclic radical with 5 to 6 ring atoms, in which 1 to 3 hetero-atoms (such as oxygen and/or sulphur and/or nitrogen) can be present in the ring system.

Very particularly preferred compounds of the formula I are those in which
 $R^1$ represents a trichloromethyl or fluorodichloromethyl radical and
 $R^2$ represents alkyl with up to 6 carbon atoms, which can optionally carry one or more substituents selected from halogen, methoxy, ethoxy and methylthio, or represents cyclohexyl, or represents phenyl which can optionally carry one or more substituents selected from halogen, nitro, methyl, trifluoromethyl and methoxy.

If, for example, fluorodichloromethanesulphenyl-N-methylamide and chlorocarbonyl isocyanate are used as starting materials for the preparation of a compound according to the invention, the course of the reaction can be represented by the following equation:

$$FCl_2C-S-NH(CH_3) + ClCO-NCO \xrightarrow[-HCl]{\Delta}$$

$$FCl_2C-SN(CH_3)-CO-NCO$$

The formula II provides a general definition of the trihalogenomethane-sulphenamides to be used as starting materials; in this formula, $R^1$ and $R^2$ preferably have those meanings which have already been mentioned as preferred in connection with the description of the compounds of the formula I.

Compounds of the general formula II which can be used according to the invention are known and can be prepared in accordance with known processes (see French Patent Specification No. 1,339,765 or Chem. Abstr. 60, 5519 (1964)). They are obtained when a trihalogenomethanesulphenyl chloride is reacted with a primary amine, for example in toluene as the solvent, in the temperature range of from +20° to 30° C. (see also the preparative examples hereinbelow).

As examples of compounds of the formula II, there may be mentioned the trichloromethane-sulphenamides, fluorodichloromethane-sulphenamides, difluorochloromethanesulphenamides or trifluoromethane-sulphenamides of methylamine, isopropylamine, butylamine, isooctylamine, stearylamine, allylamine, propargylamine, methoxyethylamine, ethylmercaptoethylamine, βββ-trifluoroethylamine, cyclopentylamine, 2-methylcyclohexylamine, benzylamine, 3-nitro-benzylamine and phenethylamine, as well as of aniline, 4-chloroaniline, 3-methoxyaniline, 3-trifluoromethylaniline, 1-naphthylamine, 2-furylamine and 4-pyridylamine.

Chlorocarbonyl isocyanate of the formula III is known from the literature (see Angew. Chem. 89, 789 (1977)) and has been described in detail. The adduct of phosgene and cyanogen chloride is first prepared over an active charcoal catalyst and is then hydrolyzed with methanesulphonic acid, giving chlorocarbonyl isocyanate in 90% yield.

The reaction according to the invention is preferably carried out in the presence of a diluent. Any of the inert solvents can be used as the diluent, such as hydrocarbons, for example toluene, chlorinated hydrocarbons, for example chlorobenzene, or ethers, for example dioxane.

The process according to the invention is carried out without addition of an acid-binding agent. Advantageously, the chlorocarbonyl isocyanate is initially introduced as a solution, and is present in excess in the reaction mixture. The molar ratio of chlorocarbonyl isocyanate to sulphenamide can vary within a range from 1:1 to 10:1, preferably from 1.1:1 to 2:1.

The reaction temperatures can be varied over a substantial range. In general the reaction is carried out, as described above, between 0° and +150° C., preferably at from 20° to 120° C.

The isolation of the compounds according to the invention is effected in a simple manner by distillation.

The N-(sulphenamido)-acyl isocyanates of the formula I can be used as intermediate products for the preparation of N-sulphenylated biurets, by addition reaction with primary or secondary amines in a temperature range of from +20° to 50° C. (see German Patent Application No. P.3049439.4 of Dec. 30, 1980 [Le A 20 708]). Interesting secondary products to be mentioned are, for example, the compounds of the formulae.

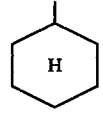

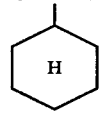

(see also the preparative examples).

These compounds can be used as plant protection agents; they have a very good fungicidal action against phytopathogenic fungi. Thus they can, for example, be used successfully for combating *Pyricularia oryzae* and *Pellicularia sasakii* in rice cultures, and surpass the effect of known commercial products.

PREPARATIVE EXAMPLES

EXAMPLE 1

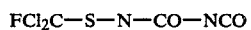
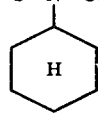

A solution of 45 g (0.2 mol) of fluorodichloromethane-sulphenyl-N-(cyclohexyl)-amide, boiling point 68° to 70° C./0.1 mm Hg, in 50 ml of chlorobenzene was added dropwise, at +10° to 20° C., to a solution of 44 g (0.4 mol) of chlorocarbonyl isocyanate in 150 ml of chlorobenzene, while cooling with ice. The reaction solution was then gradually heated to the boil, hydrogen chloride being split off from about 70°–80° C. onwards. The solution was kept at the reflux temperature for 1 hour and was then concentrated in vacuo, and the residue was distilled. 46 g of N-(fluorodichloromethane-sulphenyl)-N-(cyclohexyl)amido-carbonyl isocyanate, of boiling point 158° to 160° C./11 mm Hg, were obtained. The yield was 76% of theory.

EXAMPLE 2

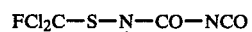

185 g (0.82 mol) of fluorodichloromethane-sulphenanilide in 100 ml of chlorobenzene were added dropwise, at +5° to 10° C., to a solution of 105 g (1 mol) of chlorocarbonyl isocyanate in 200 ml of chlorobenzene. The solution assumed a red color and an after-reaction occurred, with the temperature rising to 44° C. The solution was then heated; from about 80° C. onwards, evolution of hydrogen chloride started, with crystallization. The mixture was heated at the boil for 1 hour, the solid product (about 48 g) was filtered off, the solution was concentrated in vacuo and the residue was distilled. 25 g of N-(fluorodichloromethane-sulphenyl)-anilido-carbonyl isocyanate, of boiling point 122° to 125° C./0.2 mm Hg, were obtained. The yield was 11% of theory.

The following compounds of the general formula:

$$R^1-S-N-CO-NCO \quad (I)$$
$$\phantom{R^1-S-N}|\phantom{-CO-NCO}$$
$$\phantom{R^1-S-}R^2$$

were obtained in a similar manner:

| Compound No. | $R^1$ | $R^2$ | Boiling point (mm Hg/°C.) |
|---|---|---|---|
| 3 | $CFCl_2$ | $CH_3$ | 14/93–96 |
| 4 | $CFCl_2$ | $CH_2-CH_2-OCH_3$ | 0.1/78–80 |
| 5 | $CCl_3$ | n-$C_4H_9$ | 0.1/90–92. |

PRECURSORS

EXAMPLE 3

73 g (1 mol) of tert.butylamine were dissolved in 300 ml of toluene and 85 g (½ mol) of fluorodichloromethane-sulphenyl chloride were added dropwise, with cooling, at 20° to 30° C. The toluene solution was extracted by shaking with water and was dried over sodium sulphate and concentrated in vacuo, and the residue was distilled. 80 g (that is to say 77% of theory) of fluorodichloromethane-sulphenyl-N-(t-butyl)-amide, of boiling point 60° to 65° C./13 mm Hg, were obtained.

SECONDARY PRODUCTS

EXAMPLE 4

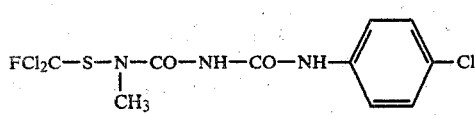

8.2 g (0.035 mol) of N-(fluorodichloromethane-sulphenyl)-N-(methyl)-amidocarbonyl isocyanate were dissolved in 60 ml of acetone and reacted, at room temperature, with a solution of 4.5 g (0.035 mol) of 4-chloroaniline in 20 mol of acetone. In the course thereof, the temperature rose to 34° C. On addition of water, 7 g of 1-fluorodichloromethylthio-1-methyl-5-(4-chlorophenyl)-biuret of melting point 148° C. were obtained; this represented 55% of theory.

This biuret as well as the others specifically named hereinabove and others producible from the novel N-(sulphenamido)-acyl isocyanates are active against plant pathogenic fungi in the usual concentrations and methods of application of such fungicides.

It will be understood that the specification and examples are illustrative but not limitative of the present invention and that other embodiments within the spirit and scope of the invention will suggest themselves to those skilled in the art.

We claim:

1. An N-(sulphenamido)-acyl isocyanate of the formula

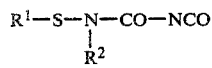

in which
   R¹ represents a trihalogenomethyl radical and
   R² represents an aliphatic, cycloaliphatic, araliphatic, aromatic, furyl or pyridyl radical.

2. A compound according to claim 1, in which
   R¹ represents a trichloromethyl, fluorodichloromethyl, difluorochloromethyl or trifluoromethyl radical and
   R² represents a straight-chain or branched alkyl radical with 1 to 18 carbon atoms, which can optionally carry one or more substituents selected from alkoxy with up to 4 carbon atoms, alkylmercapto with up to 4 carbon atoms, halogen, cyano and nitro, or represents an alkenyl or alkynyl radical, in either case with 3 to 8 carbon atoms, or represents a cycloaliphatic radical with 5 to 8 carbon atoms, which can optionally be substituted by alkyl with 1 to 4 carbon atoms, or represents an araliphatic radical with a total of 7 to 12 carbon atoms, of which the aromatic ring system can optionally carry one or more substituents selected from halogen, nitro, trifluoromethyl, cyano, alkyl with up to 4 carbon atoms and alkoxy with up to 4 carbon atoms, or represents an aromatic radical with 6 to 12 carbon atoms, which can optionally carry one or more substituents selected from halogen, nitro, cyano, alkyl with up to 4 carbon atoms, halogenalkyl with up to 4 carbon atoms, halogenalkoxy with up to 4 carbon atoms, alkylthio with up to 4 carbon atoms, halogenalkylthio with up to 4 carbon atoms and alkoxy with up to 4 carbon atoms, or represents a furyl or pyridyl.

3. A compound according to claim 1, in which
   R¹ represents a trichloromethyl or fluorodichloromethyl radical and
   R² represents alkyl with up to 6 carbon atoms, which can optionally carry one or more substituents selected from halogen, methoxy, ethoxy and methylthio, or represents cyclohexyl, or represents phenyl which can optionally carry one or more substituents selected from halogen, nitro, methyl, trifluoromethyl and methoxy.

4. A compound according to claim 1, wherein such compound is N-(fluorodichloromethane-sulphenyl)-N-(cyclohexyl)-amido-carbonyl isocyanate of the formula

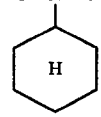

5. A compound according to claim 1, wherein such compound is N-(fluorodichloromethane-sulphenyl)-anilidocarbonyl isocyanate of the formula

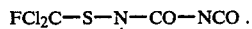
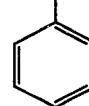

6. A compound according to claim 1, wherein such compound is N-(fluorodichloromethane-sulphenyl)-N-(methyl)-amido-carbonyl isocyanate of the formula

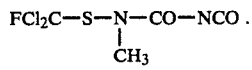

7. A compound according to claim 1, wherein such compound is N-(fluorodichloromethane-sulphenyl)-N-(2-methoxyethyl)-amido-carbonyl isocyanate of the formula

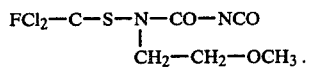

8. A compound according to claim 1, wherein such compound is N-(trichloromethane-sulphenyl)-N-(n-butyl)-amido-carbonyl isocyanate of the formula

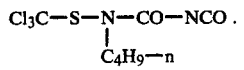

9. A process for the preparation of an N-(sulphenamido)-acyl isocyanate according to claim 1, comprising reacting a trihalogenomethanesulphenamide of the formula

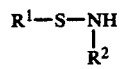

with chlorocarbonyl isocyanate of the formula

Cl—CO—NCO at a temperature from about 0° to 150° C.

10. A process according to claim 9, wherein the reaction is effected in an inert organic solvent.

11. A process according to claim 9, wherein the molar ratio of chlorocarbonyl isocyanate to sulphenamide is from about 1:1 to 10:1.

12. A process according to claim 9, wherein the solvent is a hydrocarbon, a chlorinated hydrocarbon or an ether, the molar ratio of chlorocarbonyl isocyanate to sulphenamide is from about 1.1:1 to 2:1.

* * * * *